(12) United States Patent
Atsumi

(10) Patent No.: US 6,733,459 B1
(45) Date of Patent: May 11, 2004

(54) BALLOON CATHETER FOR INTRA-AORTIC BALLOON PUMP APPARATUS

(75) Inventor: Takafumi Atsumi, Anjo (JP)

(73) Assignee: Aisin Seiki Kabushiki Kaisha, Kariya (JP)

( * ) Notice: Subject to any disclaimer, the term of this patent is extended or adjusted under 35 U.S.C. 154(b) by 0 days.

(21) Appl. No.: 09/578,685

(22) Filed: May 26, 2000

(30) Foreign Application Priority Data

May 28, 1999 (JP) ............................................ 11-149792

(51) Int. Cl.[7] ............................. A61B 5/02; A61B 5/08; A61M 29/00
(52) U.S. Cl. ..................... 600/488; 600/481; 604/96.01
(58) Field of Search ............................. 600/486, 7, 18, 600/585, 591, 488; 128/675, 899; 604/65, 96.01, 100.03, 500, 99.03, 28, 264; 60/535; 623/1.15; 607/19

(56) References Cited

U.S. PATENT DOCUMENTS

| | | | | |
|---|---|---|---|---|
| 4,407,296 A | * | 10/1983 | Anderson | 600/488 |
| 5,324,326 A | * | 6/1994 | Lubin | 600/488 |
| 5,810,735 A | * | 9/1998 | Halperin et al. | 128/899 |
| 6,013,020 A | * | 1/2000 | Meloul et al. | 600/7 |
| 6,019,729 A | * | 2/2000 | Itoigawa et al. | 600/488 |
| 6,024,704 A | * | 2/2000 | Meador et al. | 128/899 |
| 6,296,615 B1 | * | 10/2001 | Brockway et al. | 600/485 |

FOREIGN PATENT DOCUMENTS

| | | |
|---|---|---|
| JP | 61-48346 | 3/1986 |
| JP | 62-189049 | 8/1987 |

* cited by examiner

Primary Examiner—Brian L. Casler
Assistant Examiner—Roz Maiorino
(74) Attorney, Agent, or Firm—Finnegan, Henderson, Farabow, Garrett & Dunner, L.L.P.

(57) ABSTRACT

A balloon catheter for intra-aortic balloon pump which measures accurate blood pressure at the predetermined position of balloon introduced percutaneously and ensures the second lumen when catheter is in use. The balloon catheter comprised of a Y-shaped connector having gas supply port and an electric circuit, a hollow catheter tube one of which end is connected to the Y-shaped connector, a balloon one of which end is connected to the other end of the catheter tube, a hollow central tube one end of which is connected to one end of the balloon and extended through inside of the catheter tube and the balloon. The balloon catheter includes a pressure detecting element which enables to measure the pressure on the surface of a top end chip connecting the balloon and the central tube. The balloon catheter provided with a detachable connecting device transmitting output signal from the pressure detecting element to an external control device.

4 Claims, 5 Drawing Sheets

BALLOON CATHETER FOR INTRA-AORTIC BALLOON PUMP APPARATUS

BACKGROUND OF THE INVENTION

1. Field of the Invention

This invention relates to a balloon catheter for an intra-aortic balloon pump apparatus and, more particularly, to a balloon catheter for an intra-aortic balloon pump apparatus which measures accurate blood pressure at dwelled position of a catheter introduced percutaneously and ensures a hollow portion to utilize for injecting medicament fluid or extracting blood and the like when the catheter is used.

2. Description of the Related Arts

Intra-aortic balloon pumping is the supplemental circulation method aiding the cardiac function to treat the deterioration of cardiac function of a patient such as heart failure. The function of the intra-aortic balloon pumping is completed by inserting a balloon catheter into the aorta of a patient, inputting or outputting the pressurized fluid through catheter tube to said balloon using drive device complying with the cardiac pulsation, and inflating and deflating the balloon.

Double lumen balloon catheter shown in FIG. 6 is employed in a conventional arrangement of intra-aortic balloon pump. This conventional balloon catheter is comprised of central tube 2 in the hollow catheter tube 1. The central tube 2 is penetrated through a wing of Y-shaped connector, and through said catheter tube 1 and a balloon. A first lumen 3 formed between the catheter tube 1 and the central tube 2 serves as a passageway for supplying helium gas into the balloon 4. A second lumen 5 located in the hollow portion of the central tube 2 is used for a guide way for the guide wire. Since the second lumen 5 is connected to the blood vessel at the distal end, the pressure in the second lumen 5 is measured by a blood sensor secured to a proximal end via the second lumen and a separately provided extension tube. The timing of inflating and deflating the balloon is set referring to the blood pressure wave form measured by said blood sensor connected to said extension tube.

However, the obtained result from the conventional method mentioned above is insufficient to set an accurate timing of inflating and deflating the balloon complying with the cardiac pulsation. The blood pressure wave form obtained from the method above has some delay and inaccuracy compared to the original blood pressure wave form at the dwelled position of the balloon, due to the measurement at the other end of the long and narrow second lumen 5 and the separately provided extension tube.

As a solution of the problems mentioned above, a device shown in a Japan Patent Laid-open Publication S61-48346 (published on Mar. 10, 1986) is disclosed. A pressure sensor is disposed on the tip of the balloon catheter, and the signal from said pressure sensor is outputted from the patient's body to the outside thereof via the catheter according to said conventional prior art.

Another Japan Patent Laid-open Publication S62-189049 (published on Aug. 18, 1987) discloses the means utilizing the aforementioned second lumen formed in the double lumen balloon catheter. In this prior art, the catheter is first inserted percutaneously into the patient's body and then a special catheter on tip end of which a pressure sensor is provided is inserted through the second lumen of the catheter until the pressure sensor reaches to the tip end of the balloon catheter.

Above-mentioned previous prior arts have the following disadvantages. Since the method according to the Japan Patent Laid-open Publication S61-48346 shows the single lumen structure with no provision of a second lumen for inserting the guide wire to the balloon catheter into the blood vessel, the percutaneous introduction of the catheter into the patient's body is difficult.

Aforementioned catheter equipped with the pressure sensor according to Japan Patent Laid-open Publication S62-189049 requires additional time and process for supplementary introduction of said catheter with the pressure sensor into said second lumen, which becomes a disadvantage in a critical emergency case.

Since said second lumen has been occupied with said special catheter provided with a pressure sensor after the special catheter is introduced into the patient's body, the second lumen cannot be utilized when intra-aortic balloon pumping is applied. For instance, medicament fluid cannot be injected into the blood vessel through the second lumen and blood cannot be extracted when said special catheter with pressure sensor is applied.

SUMMARY OF THE INVENTION

Accordingly, an object of this invention is to enable the accurate measurement of blood pressure at predetermined position of the balloon by intra-aortic balloon pump introduced percutaneously and to ensure the second lumen with a double lumen structure.

To resolve the foregoing problems the following technical means is provided with the balloon catheter of this invention which includes: a Y-shaped connector having a gas supply port and an electric circuit, a hollow catheter tube one end of which is connected to said connector, a balloon one end of which is connected to the other end of said catheter tube, a hollow central tube inserted into said catheter and serving as a passageway for a guide wire to be inserted into a blood vessel of a patient's body, the hollow central tube being extending outwardly from the other end of said catheter tube, a top end chip provided on one tip end of the hollow central tube on the balloon side for connecting the balloon to the hollow central tube, a pressure detecting element provided in the top end chip for detecting the pressure at the outer surface of said top end chip, and a connecting device for transmitting the output signals from said pressure detecting element to an external control device.

This invention of intra-aortic balloon pump is capable of measuring the accurate blood pressure with percutaneous means and ensuring the second lumen while using the catheter.

Under this invention of intra-aortic balloon catheter, said connecting device which transmits the output signal from pressure detecting element to an external control device is capable of installation and removal of said balloon catheter.

Reducing the weight and minimizing the bulk of the Y-shaped connector reduce the undesired trouble such as bending the catheter or the cable being caught by other objects, and facilitate the handling.

This invention of intra-aortic balloon catheter is provided with the electric circuit between said pressure detecting element and said connecting device to compensate for the characteristics of said pressure detecting element.

Said electric circuit provides high-accuracy pressure sensor by compensating for the temperature, sensitivity, and zero potential.

Said central tube is provided with two hollow portions (lumen), and said signal line is disposed in one of the hollow portions.

Said signal line is avoided from contacting the blood or water content because said signal line is not disposed in the lumen that serves as a passageway for introducing a guide wire, injecting medicament fluid, or extracting the blood.

BRIEF DESCRIPTION OF THE DRAWINGS

These and other objects and features of the invention will be more apparent and more readily appreciated from the following detailed description of the preferred embodiment of the invention with the accompanying drawings, in which.

DESCRIPTION OF THE PREFERRED EMBODIMENTS

Figure 1:
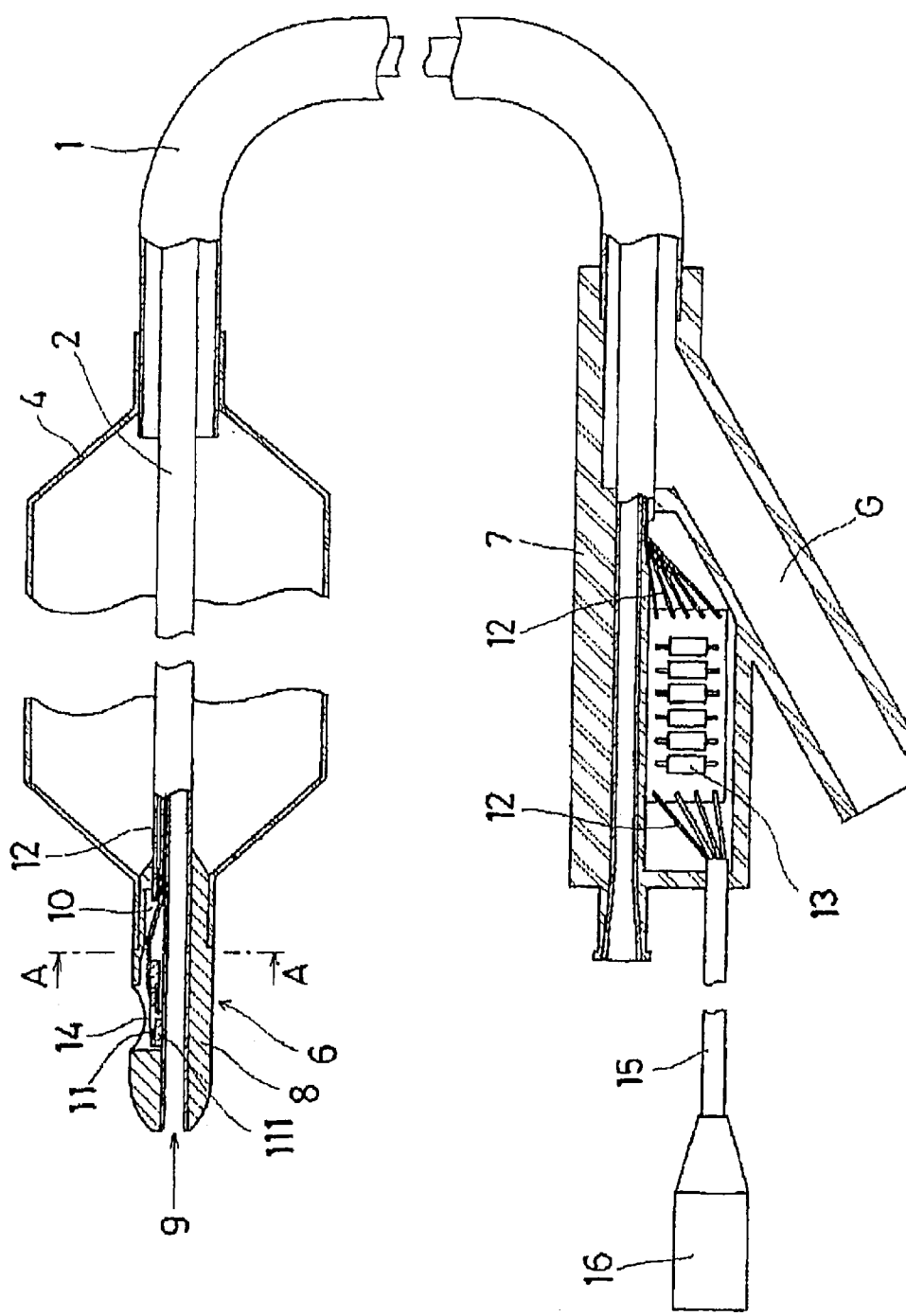
FIG. 1 is a partial cross-sectional view, illustrating an embodiment of a balloon catheter of an intra-aortic balloon pump apparatus according to this invention.

The embodiments of an intra-aortic balloon pump apparatus of this invention are described as follows referring to FIGS. 1 through 5. One end of a catheter tube 1 is connected to the bottom part of a Y-shaped connector 7. The other end of catheter tube 1 is connected to a balloon 4. A central tube 2 extends through the interior of catheter 1 and projects from the catheter 1. A top end chip 8 is disposed on one end (tip end) of the central tube 2 on the balloon side. The Y-shaped connector 7 is connected to the other end of the central tube 2. One wing of the Y-shaped connector 7 has a gas port G which supplies operation gas, such as Helium into the catheter 1.

Figure 3:
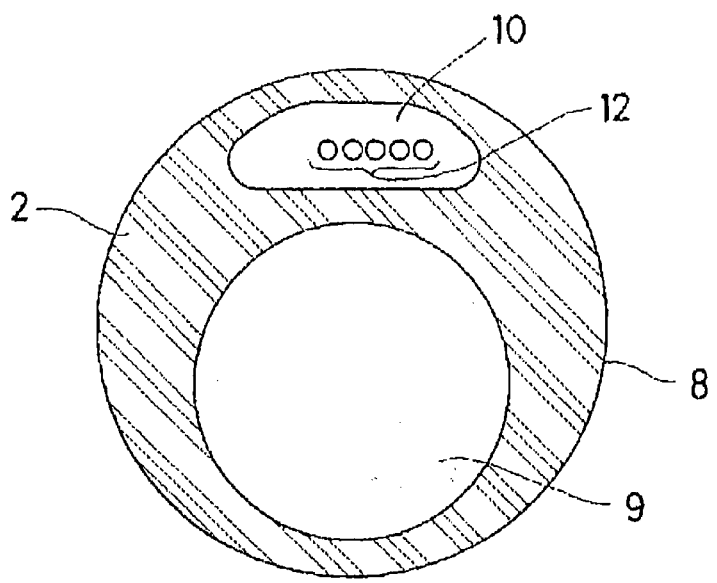
FIG. 3 is a cross-sectional view taken on line A—A of FIG. 1.

As shown in FIG. 3, the central tube 2 includes two hollow tubes: a hollow tube (lumen) 9 for inserting a guide wire and a hollow tube (lumen) 10. A pressure detecting element 11 is disposed on the outer surface of the hollow tube 9 in the top end chip 8. Signal lines 12 connected to said pressure detecting element with electric means extend through interior of the hollow tube 10, and one end of each signal line 12 is connected to a compensating circuit 13 disposed in the Y-shaped connector 7.

The pressure detecting element 11 is of a. distortion gage type which is comprised of semiconductors that detect the deformation of a diaphragm gage 14 in accordance with the changes of the pressure as electrical resistance changes. The hollow tube 10 in the central tube 2 functions as an air passageway to maintain the atmospheric pressure on the reverse side of the diaphragm gage 14. The diaphragm gage 14 is deformed by relative differential pressure between blood pressure and predetermined atmospheric pressure. Aforementioned pressure detecting element 11 is supported by block base 111 and molding material 112.

Figure 2:
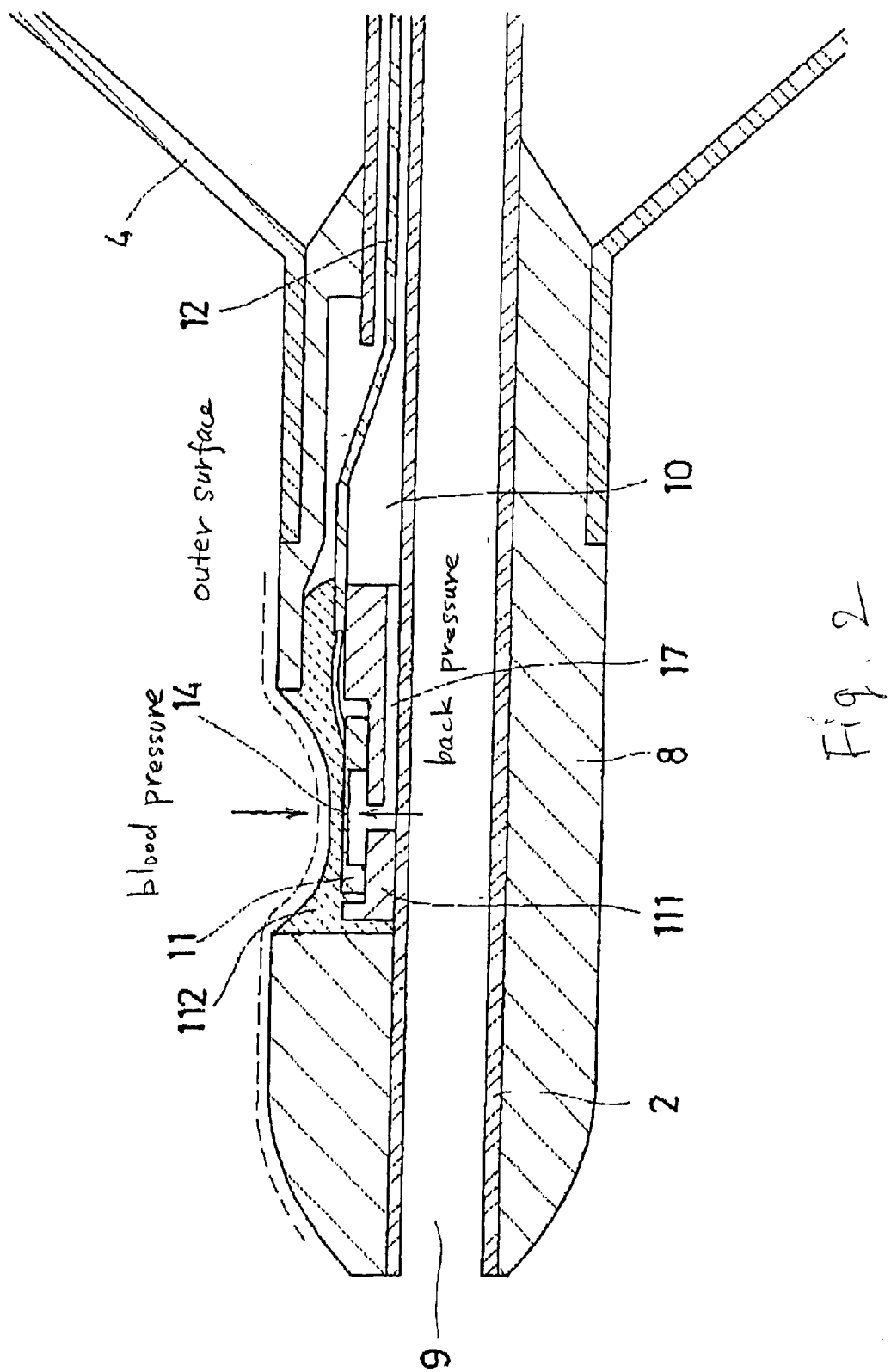
FIG. 2 is an enlarged sectional view illustrating a top end chip of this invention included in the apparatus of FIG. 1.

Shown in FIG. 2, differential pressure between blood pressure and back pressure deforms said diaphragm 14. A space 17 and the hollow tube 10 on the reverse side of the diaphragm 14 are exposed to the atmospheric pressure.

The pressure detecting element 11 and the signal line is electrically connected to the compensating circuit 13 (an electric circuit to compensate for characteristics of a pressure detecting element) end of which is stored in the Y-shaped connector 7. If manufacture accuracy improves, the compensating circuit 13 can be omitted from the apparatus. A signal output connector 16 is disposed as a signal transmission passageway, which transmits the signal to a drive device (not shown) or a blood pressure sensor (not shown) through the compensating circuit 13 and a signal cable 15.

Explaining now the operation of or use of the intra-aortic balloon pump apparatus, first, introduce a guide wire into the aorta via the patient's femoral artery by the Seldinger method until the leading end of the guide wire reaches the aortic arch. Second, insert the other end of guide wire into the central tube 2 through the aperture of the top end chip 8 on the tip of the balloon catheter, and insert the balloon catheter 6 into the patient's body along with the direction of the guide wire. The balloon 4 should be wrapped around the central tube in advance, so that outer diameter of the balloon 4 may be approximately the same diameter as the catheter tube 1. When the balloon 4 reaches to the predetermined position in the aorta, withdraw the guide wire from the central tube 2.

Afterwards, connect a fluid medicament tube and the like to the aperture in one wing of the Y-shaped connector 7 for using the hollow portion of the central tube 2 when the apparatus is actually used.

In case of not using the hollow portion in the central tube, plug in said aperture in the Y-shaped connector to prevent the back flow of blood. Intraaortic balloon pump is actuated by inputting blood pressure signal from the balloon catheter of this invention into a predetermined terminal directly, or through amplifier provided separately to supply the driving gas. A drive device and a hose should be connected to the catheter through the Y-shaped connector.

Figure 4:
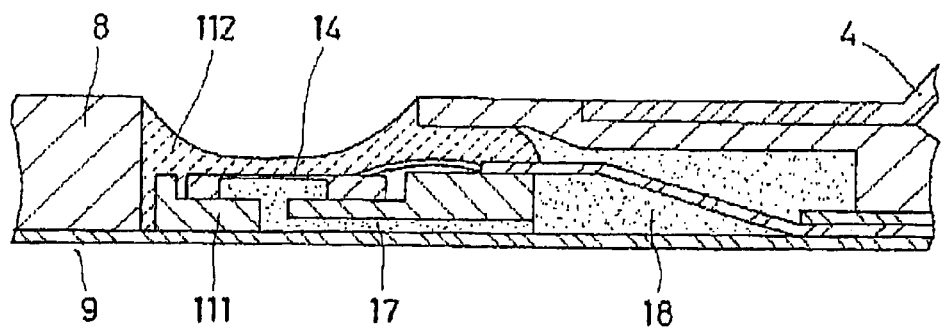
FIG. 4 is a partial cross-sectional view, illustrating a top end chip of a second embodiment of this invention.

FIG. 4 shows the second preferred embodiment. Just as the aforementioned first embodiment, a distortion gage, a pressure detecting element 11 is stored in the top end chip 8. A space 17 and a hollow tube 10 on the reverse side of a diaphragm gage 14 is maintained to the vacuum level and separated from the atmosphere.

In this case, the diaphragm gage 14 is deformed based on the absolute blood pressure. Since it is unnecessary to ensure the atmosphere passageway in a central tube 2, it is possible to embed signal lines 12, which transmit the output signal from the pressure detecting element 11, in the internal wall of the central tube 2. This integration of the central tube 2 and said signal lines 12 gives an advantage to minimize the diameter of the central tube 2. Thinner central tube 2 makes it possible to provide a thinner catheter tube 1 wrapping the outer periphery of the central tube 2, which eventually reduces any possible risk that the catheter disturbs blood circulation which causes ischemia. This is the general problem for this kind of catheter. The other components are the same as shown in the first embodiment and the explanation thereof are omitted from the description.

Figure 5:
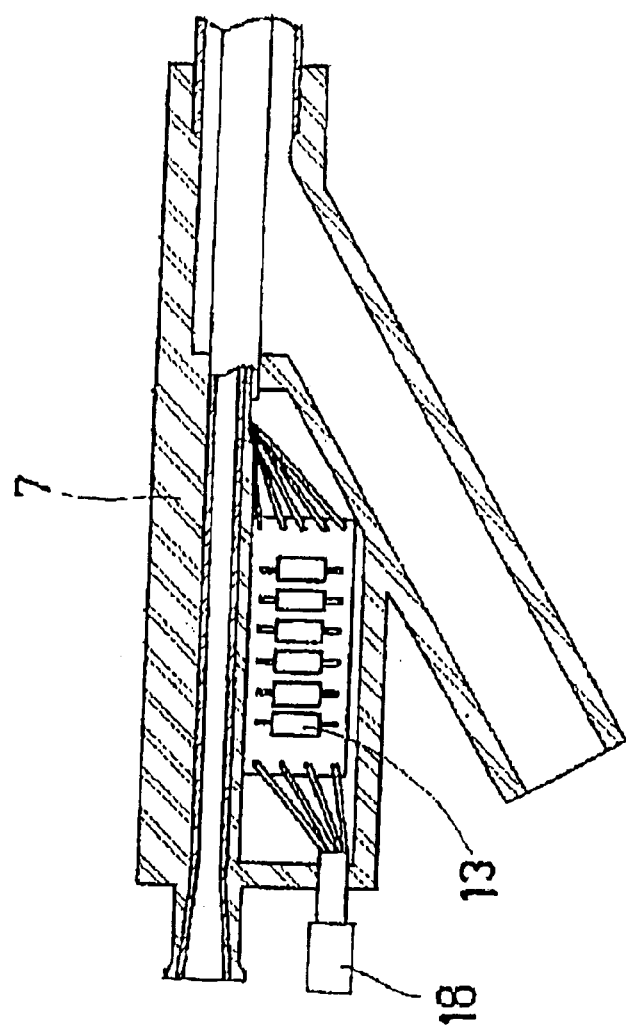
FIG. 5 is a partial cross-sectional view, illustrating a balloon catheter of a third embodiment of this invention.
Figure 5:
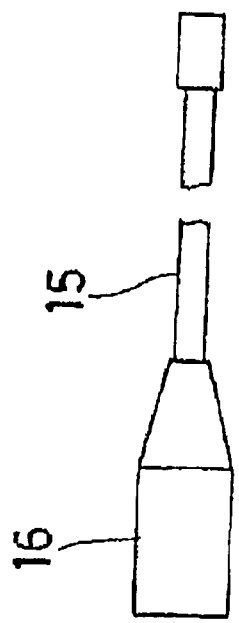
Figure 6:
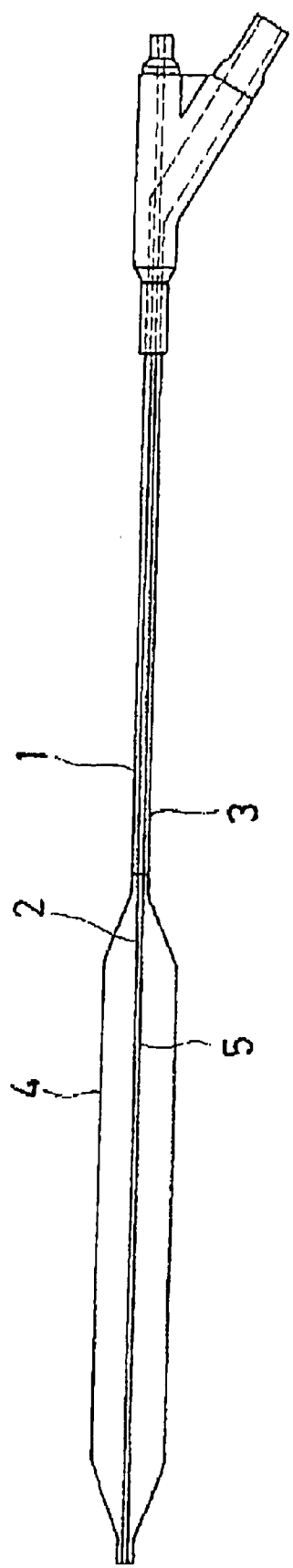
FIG. 6 is the whole view, illustrating a conventional balloon catheter.

FIG. 5 shows the third preferred embodiment. A balloon catheter comprised of the above-stated structure has disadvantage for handling when the catheter is inserted into the patient's body. This disadvantage derives from heavier weight of a Y-shaped connector since a signal cable and a device connector are suspended from the Y-shaped connector.

To resolve this problem, shown in FIG. 5, a signal cable 15 extended from the Y-shaped connector 7 is divided into two portions, the signal cable 15 and a small-sized intermediate connector 18. The intermediate connector 18 is connected to the end of the Y-shaped connector 7.

The advantage for using the intermediate connector 18 mentioned above is to reduce the weight and the bulk of the circumference of the Y-shaped connector, which enables the handling of the catheter easier while inserting the catheter into the patient's body by reducing the troubles bending the catheter or being the cable caught by other objects.

To prevent exposed conducting portion of the intermediate connector 18 from contacting the patient's body fluid, it is better to attach a waterproof cap to the intermediate connector 18 while inserting the catheter into the patient's body.

It is intended that the foregoing detailed description be regarded as illustrative rather than limiting and that it is understood that the following claims including all equivalents are intended to define the scope of the invention.

I claim:

1. A balloon catheter for an intra-aortic balloon pump comprising:

a connector having a gas supply port for supplying an operational gas to an inflatable balloon to inflate or deflate the balloon;

a catheter tube having one end connected to said connector and the other end connected to said inflatable balloon;

a hollow central tube inserted into said catheter tube and serving as a passageway for a guide wire to be inserted into a blood vessel of a patient's body, the hollow central tube extending outwardly from the other end of said catheter tube;

a top end chip provided on one tip end of the hollow central tube, said tip end located on the end of the hollow central tube in the direction of the inflatable balloon for connecting the balloon to the hollow central tube;

a pressure-sensing molding material member provided on an outer surface of the hollow central tube in the top end chip, the pressure-sensing molding material member being deformed by blood pressure inwardly of a radial direction of the top end chip;

a blood pressure detecting element, being a distortion gage type comprising semiconductors that detect deformation of a diaphragm gage in accordance with a deformation of the pressure sensing solid member as electrical resistance change, disposed on an outer surface of the hollow central tube in the top end chip, wherein said pressure sensing molding material member, when deformed by the blood pressure, contacts only said blood pressure detecting element; and a connecting device for transmitting output signals from said pressure detecting element to an external control device via a signal line disposed in the catheter tube.

2. A balloon catheter for an intra-aortic balloon pump according to claim 1, wherein the connector is Y-shaped and the connecting device is detachably connected with a first wing of the Y-shaped connector.

3. The balloon catheter according to claim 2, wherein an electric circuit compensating for the characteristics of said pressure detecting element is provided in the Y-shaped connector between said pressure detecting element and said connecting device.

4. The balloon catheter according to claim 3, wherein the Y-shaped connector includes the gas supply port in a second wing and the electric circuit in the first wing.

* * * * *